United States Patent
Hackel et al.

(10) Patent No.: US 9,701,600 B2
(45) Date of Patent: Jul. 11, 2017

(54) PLANT FOR THE PRODUCTION OF METHANOL FROM SYNTHESIS GAS RICH IN INERTS

(71) Applicant: Air Liquide Global E&C Solutions Germany GmbH, Frankfurt am Main (DE)

(72) Inventors: Philipp Marius Hackel, Frankfurt am Main (DE); Rainer Morgenroth, Hattstedt (DE); Andreas Bormann, Frankfurt am Main (DE); Veronika Gronemann, Frankfurt am Main (DE)

(73) Assignee: AIR LIQUIDE GLOGAL E&C SOLUTIONS GERMANY GMBH, Frankfurt am Main (DE)

( * ) Notice: Subject to any disclaimer, the term of this patent is extended or adjusted under 35 U.S.C. 154(b) by 0 days.

(21) Appl. No.: 14/956,404

(22) Filed: Dec. 2, 2015

(65) Prior Publication Data
US 2016/0083319 A1      Mar. 24, 2016

Related U.S. Application Data (62) Division of application No. 14/111,205, filed as application No. PCT/EP2012/001256 on Mar. 22, 2012, now Pat. No. 9,296,672.

(30) Foreign Application Priority Data

Apr. 15, 2011   (DE) .................. 10 2011 017 300

(51) Int. Cl.
*B01J 19/00*     (2006.01)
*B01J 19/24*     (2006.01)
(Continued)

(52) U.S. Cl.
CPC ............ *C07C 29/152* (2013.01); *B01J 19/245* (2013.01); *C10J 3/82* (2013.01); *B01J 2219/24* (2013.01);
(Continued)

(58) Field of Classification Search
CPC . B01J 19/00; B01J 19/24; B01J 19/245; B01J 2219/24; C07C 29/00; C07C 29/15;
(Continued)

(56) References Cited

U.S. PATENT DOCUMENTS 4,326,041 A    4/1982  Baehnisch
4,910,228 A    3/1990  Lywood
(Continued)

FOREIGN PATENT DOCUMENTS

CN    1045092 A    9/1990
CN    1211561 A    3/1999
(Continued)

OTHER PUBLICATIONS

"Ullmann's Encyclopedia of Industrial Chemistry: Gas Production, 2. Processes", Published Online: Oct. 15, 2011, DOI: 10.1002/14356007.001, p. 423-482.
(Continued)

*Primary Examiner* — Natasha Young
(74) *Attorney, Agent, or Firm* — Leydig, Voit & Mayer, Ltd.

(57) ABSTRACT

During the production of methanol from inert-rich syngas, a catalytic pre-reactor is installed upstream of the single- or multi-stage synthesis loop, a first part of the syngas being converted to methanol in the catalytic pre-reactor. An inert gas separation stage, for example a pressure swing adsorption system or a membrane system, can be connected downstream of the synthesis loop, whereby a hydrogen-enriched syngas stream can be returned to the synthesis loop.
(Continued)

In the processing of methane-rich syngas, the inert gas separation stage may also have an autothermal reformer in which methane is converted to carbon oxides and hydrogen, which are also returned into the synthesis loop.

17 Claims, 6 Drawing Sheets (51) Int. Cl.
| | |
|---|---|
| *C07C 29/00* | (2006.01) |
| *C07C 29/15* | (2006.01) |
| *C07C 29/151* | (2006.01) |
| *C07C 29/152* | (2006.01) |
| *C07C 31/00* | (2006.01) |
| *C07C 31/02* | (2006.01) |
| *C07C 31/04* | (2006.01) |
| *C10J 3/00* | (2006.01) |
| *C10J 3/72* | (2006.01) |
| *C10J 3/82* | (2006.01) |

(52) U.S. Cl.
CPC .. *C10J 2300/093* (2013.01); *C10J 2300/0916* (2013.01); *Y02E 50/18* (2013.01); *Y10T 29/49716* (2015.01)

(58) Field of Classification Search
CPC ............... C07C 29/151; C07C 29/152; C07C 31/00–31/04; C10J 3/00; C10J 3/72; C10J 3/82; C10J 2300/00; C10J 2300/09; C10J 2300/0913; C10J 2300/0916; C10J 2300/093; Y02E 50/00; Y02E 50/10; Y02E 50/18; Y10T 29/00; Y10T 29/49; Y10T 29/49716
See application file for complete search history.

(56) References Cited

U.S. PATENT DOCUMENTS

| | | |
|---|---|---|
| 5,827,901 A | 10/1998 | Koenig et al. |
| 6,258,860 B1 | 7/2001 | Weedon et al. |
| 6,809,121 B1 | 10/2004 | Rytter et al. |
| 2005/0020700 A1 | 1/2005 | Bahnisch |
| 2008/0269359 A1 | 10/2008 | Bell |
| 2009/0018220 A1 | 1/2009 | Fitzpatrick |
| 2009/0186952 A1 | 7/2009 | Steynberg et al. |
| 2011/0065966 A1* | 3/2011 | Mueller ................ B01J 8/0488 568/840 |
| 2012/0129958 A1 | 5/2012 | Bormann et al. |

FOREIGN PATENT DOCUMENTS

| | | |
|---|---|---|
| CN | 101184714 A | 5/2008 |
| DE | 1296133 B | 5/1969 |
| DE | 2934332 A1 | 3/1981 |
| DE | 10156092 A1 | 6/2003 |
| DE | 112006001310 | 4/2008 |
| DE | 102007040707 A1 | 3/2009 |
| DE | 102009034551 A1 | 2/2011 |
| EP | 0790226 A1 | 8/1997 |
| EP | 1016643 A1 | 7/2000 |
| EP | 1819653 A1 | 8/2007 |
| WO | WO 9614279 A1 | 5/1996 |
| WO | WO 2009007032 A1 | 1/2009 |
| WO | WO 2011009437 A2 | 1/2011 |

OTHER PUBLICATIONS

Ullmann's Encyclopedia of Industrial Chemistry, Sixth Edition, Dec. 1998 Electronic Release, Chapter "Methanol", Sub-Chapter 5.2 "Synthesis".

* cited by examiner

PLANT FOR THE PRODUCTION OF METHANOL FROM SYNTHESIS GAS RICH IN INERTS

CROSS-REFERENCE TO RELATED APPLICATIONS

This application is a division of U.S. application Ser. No. 14/111,205, filed Oct. 11, 2013, which was a U.S. national stage application under 35 U.S.C. §371 of International Application No. PCT/EP2012/001256, filed on Mar. 22, 2012, claiming benefit to German Patent Application No. DE 10 2011 017 300.5 filed on Apr. 15, 2011. The international application was published in German on Oct. 18, 2012, as WO 2012/139703 A1 under PCT Article 21(2).

FIELD

This invention relates to a process for the production of methanol and to a plant for carrying out this process. In particular, the invention relates to a process for the conversion of synthesis gas with a high content of inert components to methanol, as it is obtained for example by gasification of natural gas with oxygen-enriched air or by gasification of biomass or coal with a gas containing oxygen. The invention furthermore relates to a method for retrofitting an existing plant for the production of methanol from the operation with synthesis gas low in inerts to the operation with synthesis gas rich in inerts.

BACKGROUND

Processes for the production of methanol by catalytic conversion of synthesis gas containing hydrogen and carbon oxides have long since been known to those skilled in the art. For example in Ullmann's Encyclopedia of Industrial Chemistry, Sixth Edition, 1998 Electronic Release, Chapter "Methanol", Sub-chapter 5.2 "Synthesis", various basic processes for the production of methanol are described.

A more advanced, two-stage process for the production of methanol is known for example from EP 0 790 226 B1. The methanol is produced in a cyclic process in which a mixture of fresh and partly reacted synthesis gas first is supplied to a water-cooled reactor and then to a gas-cooled reactor, in each of which the synthesis gas is converted to methanol on a copper-based catalyst. The methanol produced in the process is separated from the synthesis gas to be recirculated, which then is countercurrently passed through the gas-cooled reactor as coolant and preheated to a temperature of 220 to 280° C., before it is introduced into the first synthesis reactor. A part of the synthesis gas to be recirculated is removed from the process as purge stream (so-called purge), in order to prevent that inert components are enriched within the synthesis cycle. This measure is also taught in the unexamined German Patent Application DE 2934332 A1 and in the European Patent Application EP 1016643 A1.

In the two methods described above it is disadvantageous that when processing synthesis gases with a high content of inert components the cycle ratio must be increased, as due to the lower partial pressures of the reactants the conversion to methanol per passage through the synthesis reactor is lower than with synthesis gas low in inerts. This leads to an increase of the required compressor capacity and—with a given production capacity for methanol—to larger dimensions for apparatuses and conduits.

Inert components on the one hand are understood to be inorganic gas constituents such as nitrogen or inert gases, which are obtained for example from the production of synthesis gas proceeding from natural gas with corresponding constituents. Such natural gases are obtained for example from Asian deposits. In the gasification of natural gases with air or oxygen-enriched air, as it is discussed recently above all for smaller plants which are located far away from air separation systems for producing oxygen, there are also obtained synthesis gases rich in nitrogen; this is proposed for example in the International Patent Application WO 96/14279 A1. On the other hand, non-converted methane, which during the gasification of natural gas or coal can be contained in the synthesis gas product, is regarded as an inert gas in the sense of the methanol synthesis, as it is not converted further in this synthesis.

The problems of processing of synthesis gases rich in inerts in the methanol synthesis have been known for quite some time. Various technical solutions have already been proposed, which could, however, not gain acceptance due to their disadvantages.

In the unexamined German Patent Application DE 1296133 B it is proposed, for example, to treat the raw synthesis gas containing inert components such as nitrogen, methane or argon by a xylene wash, whereby distinct reductions of the contents of the inert components should be achieved. Here, it is disadvantageous that before entry into the gas scrubber the temperature of the synthesis gas must be lowered to −10 to −30° C., in order to significantly lower the partial pressures of the inert components. This results in a high loss of exergy. In addition, a laden absorbent is obtained, which must be aftertreated and which contains the component xylene foreign to the process of the methanol synthesis.

A similar technical teaching can be taken from the unexamined German Patent Application DE 10156092 A1, in which it is proposed to provide an absorption stage upstream of each catalytic reaction system for the production of methanol, which contains a methanol synthesis catalyst as absorbent and which is operated at a temperature which lies below the temperature for the catalytic conversion to methanol. As absorbent an auxiliary substance inherent to the process is employed, but the two above-mentioned disadvantages of a required decrease in temperature and an aftertreatment or disposal of the absorbent still exist.

A method for the production of methanol from a synthesis gas obtained from the autothermal gasification of natural gas, containing 20 to 50% each of hydrogen, carbon monoxide and methane, is described in the patent application EP 1819653 A1. There are not taken any particular measures with respect to the methane remaining in the reactor product of the methanol synthesis reactor, but the hydrogen content is increased by means of conversion, the hydrogen—possibly with the likewise produced carbon dioxide—then is separated and again charged to the methanol synthesis reactor. The partial pressures of the reactants are increased by this measure, but the cycle stream remains high due to the high content of inert components.

In general, it should therefore be noted that no satisfactory technical solution of the object has been found so far, although the problem, as illustrated, already exists for quite some time. In addition, many of the above discussed methods aim at reducing the purge stream containing inert components by a corresponding treatment as far as possible.

SUMMARY

In an embodiment, the present invention provides a plant for the production of methanol from a synthesis gas containing hydrogen, one or more carbon oxides, and one or more inert components, the plant comprising: a methanol pre-reactor in which a first part of the carbon oxides is catalytically converted to methanol; a methanol main reactor in which a second part of the carbon oxides is catalytically converted to methanol; a first separator, downstream of the methanol pre-reactor, configured to separate the methanol from the synthesis gas; a second separator, downstream of the methanol main reactor, configured to separate further methanol from the synthesis gas; a conduit configured to recirculate a synthesis gas cycle stream to the methanol main reactor; an inert gas separation stage; a conduit configured to supply synthesis gas from the methanol main reactor to the inert gas separation stage; a conduit configured to discharge a purge stream from the inert gas separation stage; and a conduit configured to recirculate a recirculation stream, depleted of one or more inert components, to the methanol main reactor.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Embodiments of the present invention avoid the above-mentioned disadvantages and provides a more economic and technically more easily feasible process for the production of methanol by using synthesis gas rich in inerts as educt gas, which in particular is characterized by a low energy demand, smaller apparatus dimensions and the avoidance of auxiliary substances foreign to the process.

An aspect of the invention provides a process for the production of methanol from a synthesis gas containing hydrogen and carbon oxides with a high content of inert components the following process steps are performed in detail:

a first synthesis gas stream is passed as feed stream through at least one methanol pre-reactor, in which a part of the carbon oxides is catalytically converted with hydrogen to obtain methanol; the methanol produced is separated, and thus a second synthesis gas stream is obtained;

the second synthesis gas stream is passed through at least one methanol main reactor, in which a further part of the carbon oxides is catalytically converted with hydrogen to obtain methanol; the methanol produced is separated, and thus a third synthesis gas stream is obtained;

the third synthesis gas stream is divided into a fourth synthesis gas stream and a fifth synthesis gas stream, wherein the fourth synthesis gas stream is recirculated to the methanol main reactor and in this way forms an inner synthesis cycle;

the fifth synthesis gas stream is supplied to at least one inert gas separation stage, wherein a sixth recirculation stream depleted of inert components and a purge stream enriched in inert components are obtained;

the sixth recirculation stream depleted of inert components is recirculated to the methanol main reactor or reactors, and in this way an outer synthesis cycle is formed.

Surprisingly, it was found that the methanol pre-reactor upstream of the methanol main reactor advantageously cooperates with the methanol main reactor and the separation of inert synthesis gas components downstream of the methanol main reactor, because due to the reaction of a part of the synthesis gas in the pre-reactor to methanol the gas load of the synthesis cycle is reduced distinctly. Therefore, the synthesis gas components separated from the purge gas stream, the so-called purge, can be recirculated without a dramatic rise in the required compressor capacity, the dimensions of the apparatuses and conduits used in the synthesis cycle, and the amount of catalyst required in the methanol main reactor.

According to a preferred aspect of the invention it is provided that the inert gas separation stage comprises a pressure swing adsorption system or a membrane system. In this way, a gas stream enriched in hydrogen and at the same time depleted of inert components can be obtained and be recirculated to the first methanol main reactor.

Advantageously, the inert gas separation stage can comprise an autothermal reformer, preferably along with a pressure swing adsorption system The first synthesis gas stream advantageously can be obtained by gasification of natural gas or biomass with a gas containing oxygen. Alternatively, the first synthesis gas stream also can be obtained by gasification of coal with a gas containing oxygen. In the last-mentioned case, the synthesis gas obtained frequently is particularly rich in methane, so that in particular in this case it is recommendable that the inert gas separation stage comprises an autothermal reformer, since methane is converted in the same and can thus be obtained as synthesis gas.

The methanol streams separated after the methanol pre-reactor or after the methanol main reactor or reactors can be supplied, preferably jointly, to the methanol product processing known per se. The same usually comprises one or more distillation steps, so that finally pure methanol can be obtained as product.

In a further aspect of the invention, the methanol pre-reactor can be operated adiabatically or in a cooled, preferably water-cooled manner. In the water-cooled operation of the methanol pre-reactor the exothermicity of the methanol synthesis reaction can be utilized for the steam generation.

In particular when charging the methanol pre-reactor with low-hydrogen synthesis gases of a low stoichiometric number SN, which is defined by $$SN=((c(H_2)-c(CO_2))/((c(CO)+c(CO_2)))$$

the methanol synthesis reaction involves a high release of heat. Therefore, in a further advantageous aspect of the invention it is provided to equip the methanol pre-reactor with its own synthesis gas recirculation. After separation of the methanol produced in the methanol pre-reactor, not the entire synthesis gas stream leaving the methanol pre-reactor, but merely a partial stream therefore is guided to the methanol main reactor and the remaining part of the synthesis gas stream is recirculated to before the methanol pre-reactor. In this way, the exothermicity of the conversion is limited, which leads to a prolonged useful life or service life of the methanol synthesis catalyst used in the methanol pre-reactor.

The methanol main reactors can be operated in a water-cooled, gas-cooled or adiabatic manner. Due to the high reaction enthalpy in the methanol synthesis, the cooled reactor operation is recommendable.

According to a preferred aspect of the invention two methanol main reactors are present in the synthesis cycle, wherein the first methanol main reactor in flow direction is operated in a water-cooled manner and the second methanol main reactor in flow direction is operated in a gas-cooled manner. As cooling gas, the synthesis gas entering into the synthesis cycle can be used in the second methanol main reactor.

The invention also extends to a plant for the production of methanol from a synthesis gas containing hydrogen and carbon oxides with a high content of inert components, in particular for carrying out a process according to any of the preceding claims, with one or more methanol pre-reactors in which a first part of the carbon oxides is catalytically converted to methanol, with one or more methanol main reactors in which a further part of the carbon oxides is catalytically converted to methanol, a separator downstream of the methanol pre-reactor or pre-reactors for separating the methanol from the synthesis gas, a further separator downstream of the methanol main reactor or reactors for separating further methanol from the synthesis gas, and conduits for recirculating a synthesis gas cycle stream to at least one methanol main reactor. The plant according to the invention furthermore comprises an inert gas separation stage as well as conduits for supplying synthesis gas from the methanol main reactor or reactors to the inert gas separation stage, conduits for discharging a purge stream from the inert gas separation stage, and conduits for recirculating a recirculation stream depleted of inert components to the methanol main reactor or reactors.

The invention furthermore relates to a method for retrofitting an existing plant for the production of methanol with one or more methanol main reactors within an inner synthesis cycle from the operation with synthesis gas low in inerts to the operation with synthesis gas rich in inerts. The retrofitting method according to the invention comprises the following measures:

Upstream of the first methanol main reactor a methanol pre-reactor is provided.

Downstream of the last methanol main reactor an inert gas separation stage is provided, and by recirculating a recirculation stream depleted of inert components to the methanol main reactor or reactors by means of corresponding conduits an outer synthesis cycle is formed, wherein the methanol pre-reactor or pre-reactors and the inert gas separation stage are located outside the inner synthesis cycle.

Figure 1:
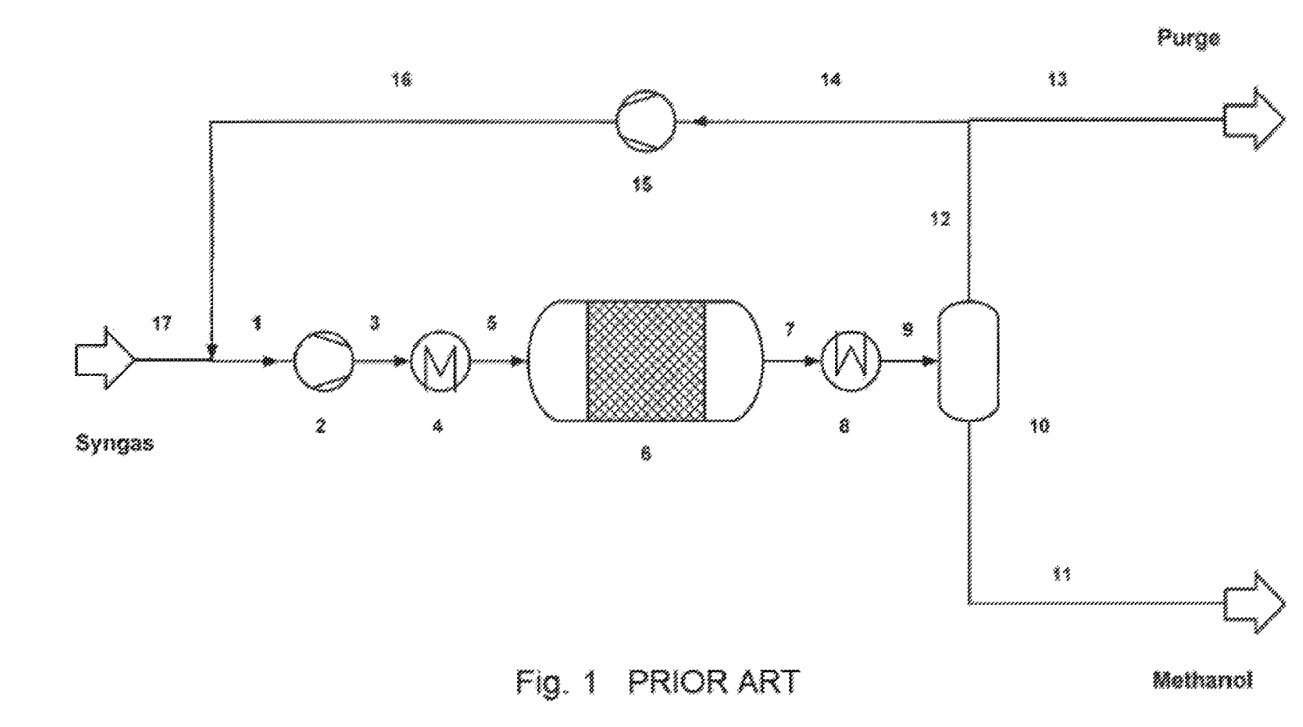
FIG. 1 schematically shows a plant for the production of methanol by a process according to the prior art as described above.

In the plant for the methanol synthesis by a prior art process, which is schematically shown in FIG. 1 in a simplified form, a synthesis gas stream containing hydrogen and carbon oxides is supplied via conduit 1 to a compressor 2 and by the same brought to the reaction pressure of typically 5 to 10 MPa. Compressor 2 and compressor 15 can technically be coupled with each other. Via conduit 3, the compressed synthesis gas stream is supplied to a heat exchanger 4 and in the same brought to the reaction temperature, wherein the heat exchange mostly is effected against the hot product gas stream from the synthesis reactor (not shown in FIG. 1). Via conduit 5, the preheated synthesis gas stream enters into the methanol main reactor 6, where at temperatures between 200 and 300° C. the partial conversion of hydrogen with carbon oxides is effected on a copper-based methanol synthesis catalyst, wherein a product mixture is obtained, which contains methanol and non-converted synthesis gas. Various copper-based methanol synthesis catalysts are commercially available, for example from Süd-Chemie AG, München. The space velocity in the synthesis reactor typically is 10000 to 30000 $h^{-1}$. In the schematic representation of FIG. 1, the methanol main reactor is shown as a one-stage reactor; preferably, however, a plurality of series-connected methanol main reactors are provided in the practical configuration.

Via conduit 7, the product mixture is discharged from the methanol main reactor. After cooling in the heat exchanger 8, where cooling to temperatures distinctly below the dew point for methanol and water, preferably between 30 and 60° C. is effected, the product mixture is delivered via conduit 9 into the separator 10, where methanol is separated as liquid, water-containing crude methanol and supplied to the further product processing via conduit 11. The gas product obtained in the separator is discharged via conduit 12 and separated into a purge stream (purge), which is discharged via conduit 13, and a cycle stream, which is supplied to the cycle compressor 15 via conduit 14. Via the purge stream, inert components are discharged from the process, but not in enriched form. Via conduit 16, the cycle stream is recirculated to the synthesis reactor 6 and in this way a synthesis cycle is formed, wherein fresh synthesis gas is supplied via conduit 17 and combined with the cycle stream. The ratio of the molar flow rates of cycle stream to fresh gas stream is referred to as cycle ratio.

Figure 2:
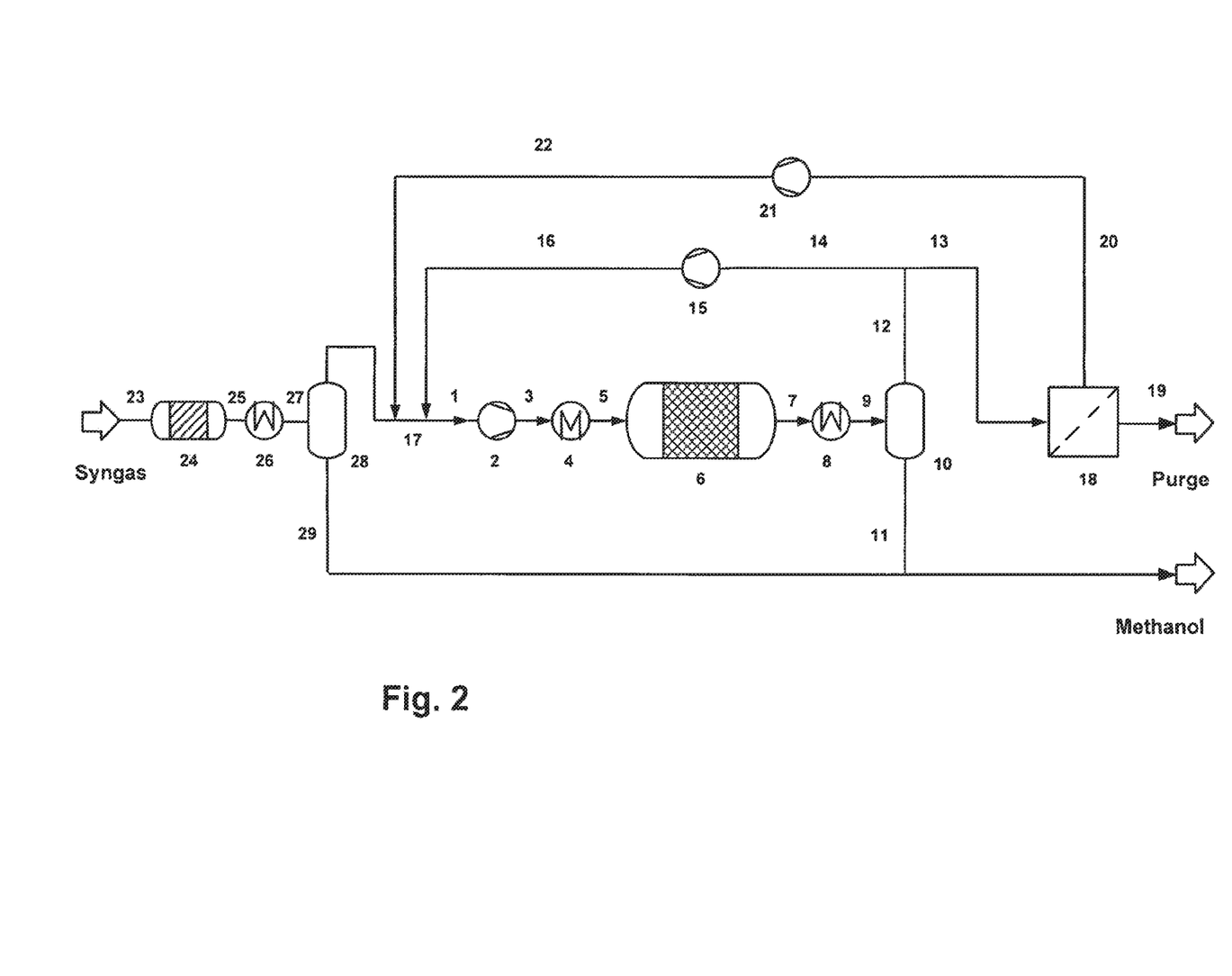
FIG. 2 schematically shows a plant for the production of methanol according to a first preferred embodiment of the invention.

In the plant shown in FIG. 2, which represents a preferred embodiment of the invention, the synthesis gas fresh gas stream initially is passed via conduit 23 to a methanol pre-reactor 24. This is an adiabatic fixed-bed reactor filled with a granular, copper-based methanol synthesis catalyst. Possibly, the synthesis gas must still be heated and compressed before entry into the methanol pre-reactor, which is not shown in FIG. 2. The reactor inlet temperature into the methanol pre-reactor lies between 190 and 250° C., the reaction pressure typically is 5 to 10 MPa. The space velocity in the methanol pre-reactor typically is 5000 to 15000 $h^{-1}$. There can be used the same catalyst type of the copper-based methanol synthesis catalyst as in the methanol main reactor; this has logistic advantages in operation of a plant by the method according to the invention. It can, however, also be advantageous to use a copper-based methanol synthesis catalyst with a higher synthesis activity as compared to the methanol main reactor. Via conduit 25, the product mixture is discharged from the methanol pre-reactor, in the heat exchanger 26 cooled to temperatures distinctly below the dew point for methanol and water, preferably between 30 and 60° C., and via conduit 27 supplied to a separator 28. In the same, methanol is separated as liquid, water-containing crude methanol and via conduit 29 supplied to the further product processing. Preferably, the further processing is effected along with the crude methanol obtained in the separator 10 and discharged from the methanol main reactor via conduit 11.

When the conversion of the synthesis gas to methanol in the methanol pre-reactor 24 is limited, it can be expedient to omit the heat exchanger 26 and the separator 28 and guide the synthesis gas containing only a small amount of methanol directly to the methanol main reactor via conduit 17.

As a further difference to the prior art process shown in FIG. 1, the purge stream as shown in FIG. 2 is not discharged from the process via conduit 13, but supplied to a pressure swing adsorption system 18. The mode of function and the operating conditions of such system are known per se to the skilled person. In said system there is obtained a synthesis gas stream depleted of hydrogen and enriched in inert components, which is removed from the process via conduit 19 (purge). Furthermore, there is obtained a synthesis gas stream enriched in hydrogen, which via conduit 20, compressor 21 and conduit 22 is recirculated upstream of the methanol main reactor, whereby an outer synthesis cycle is formed.

Figure 3:
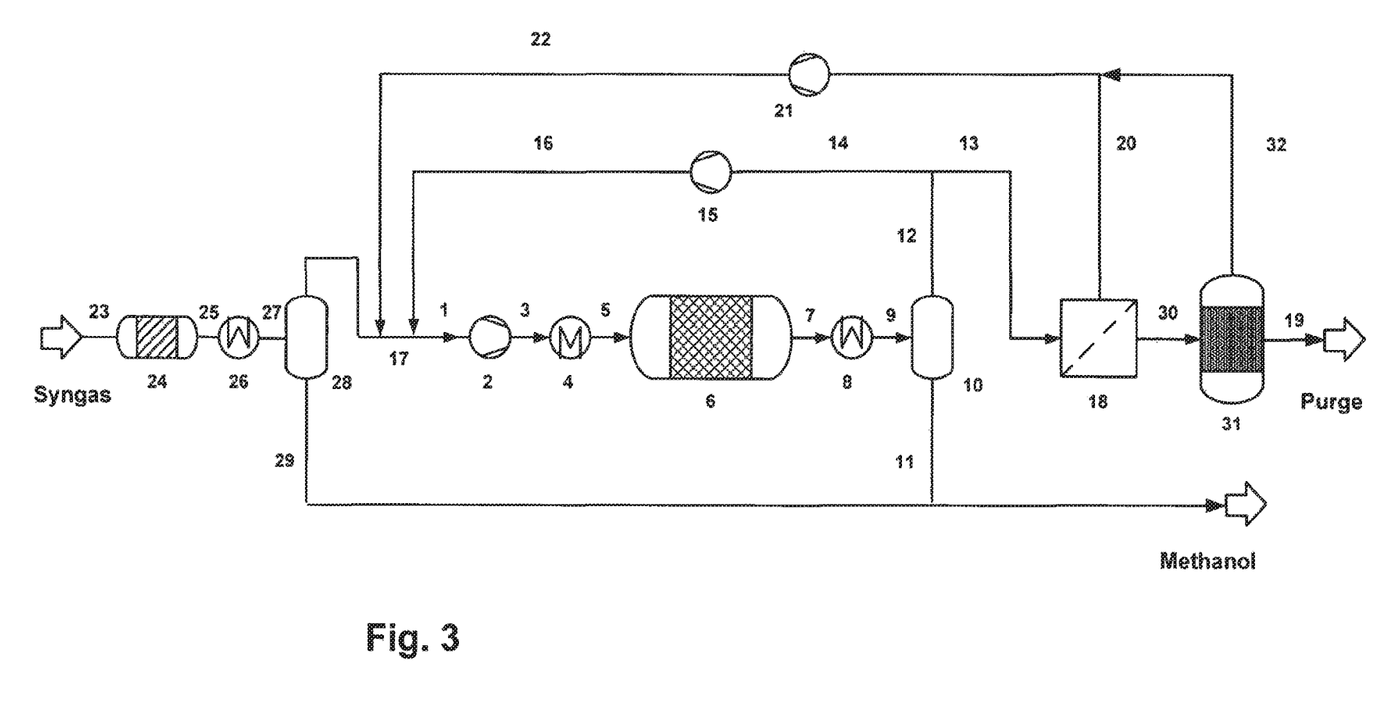
FIG. 3 schematically shows a plant for the production of methanol according to a second preferred embodiment of the invention.
Figure 4:
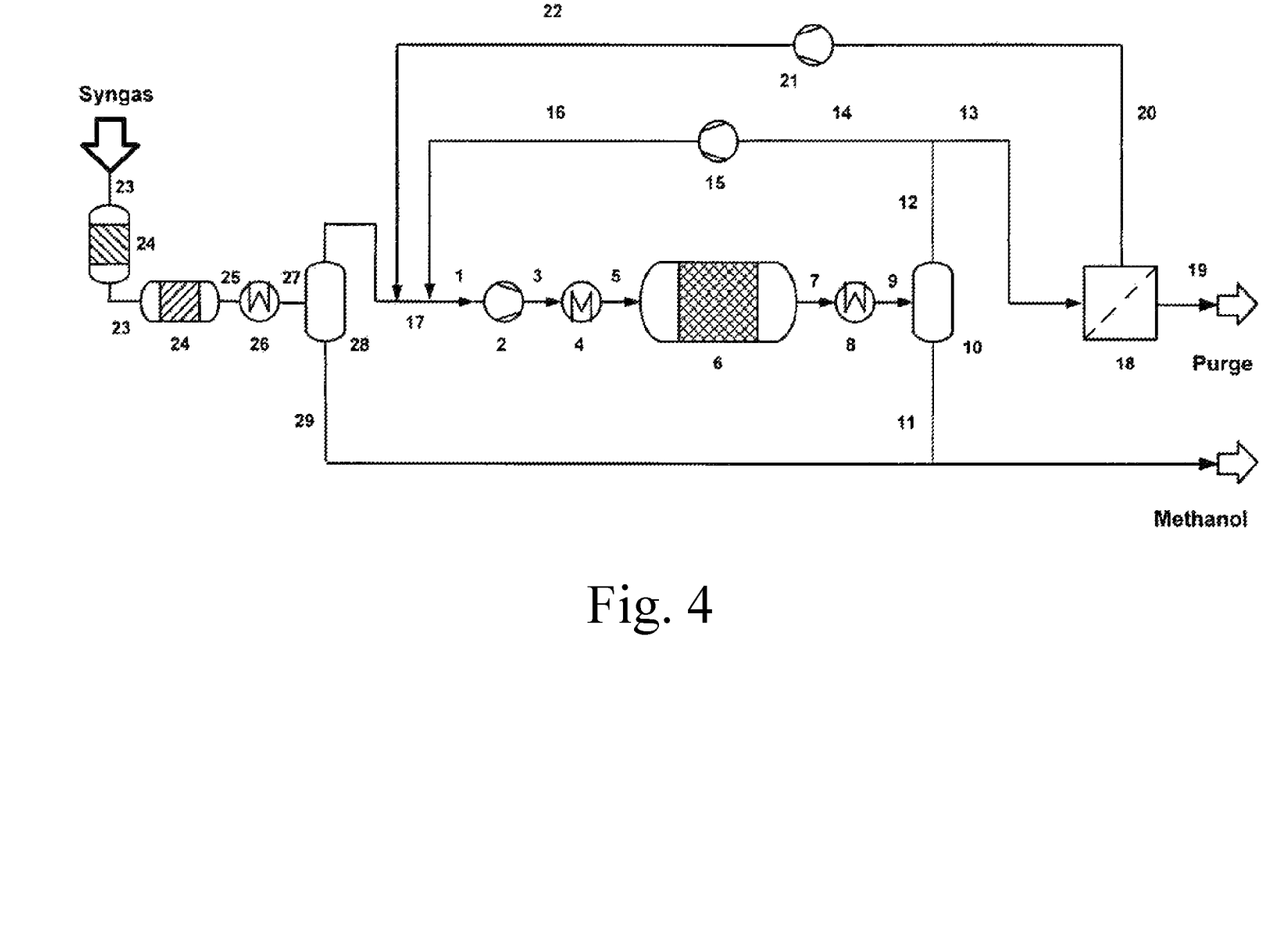
FIG. 4 schematically shows a plant for the production of methanol according to a third preferred embodiment of the invention, having a first and a second methanol pre-reactor.
Figure 5:
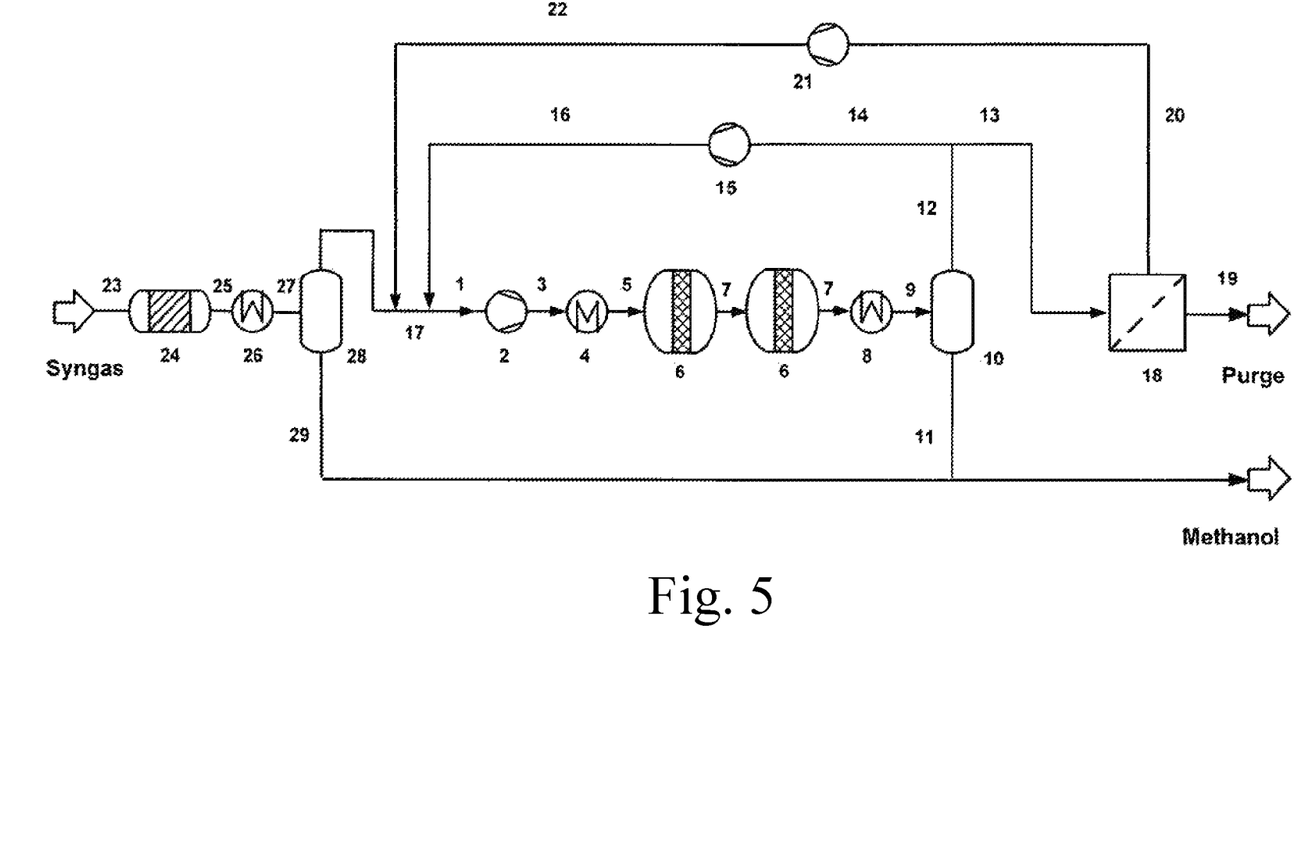
FIG. 5 schematically shows a plant for the production of methanol according to a fourth preferred embodiment of the invention, having a first and a second methanol main reactor.
Figure 6:
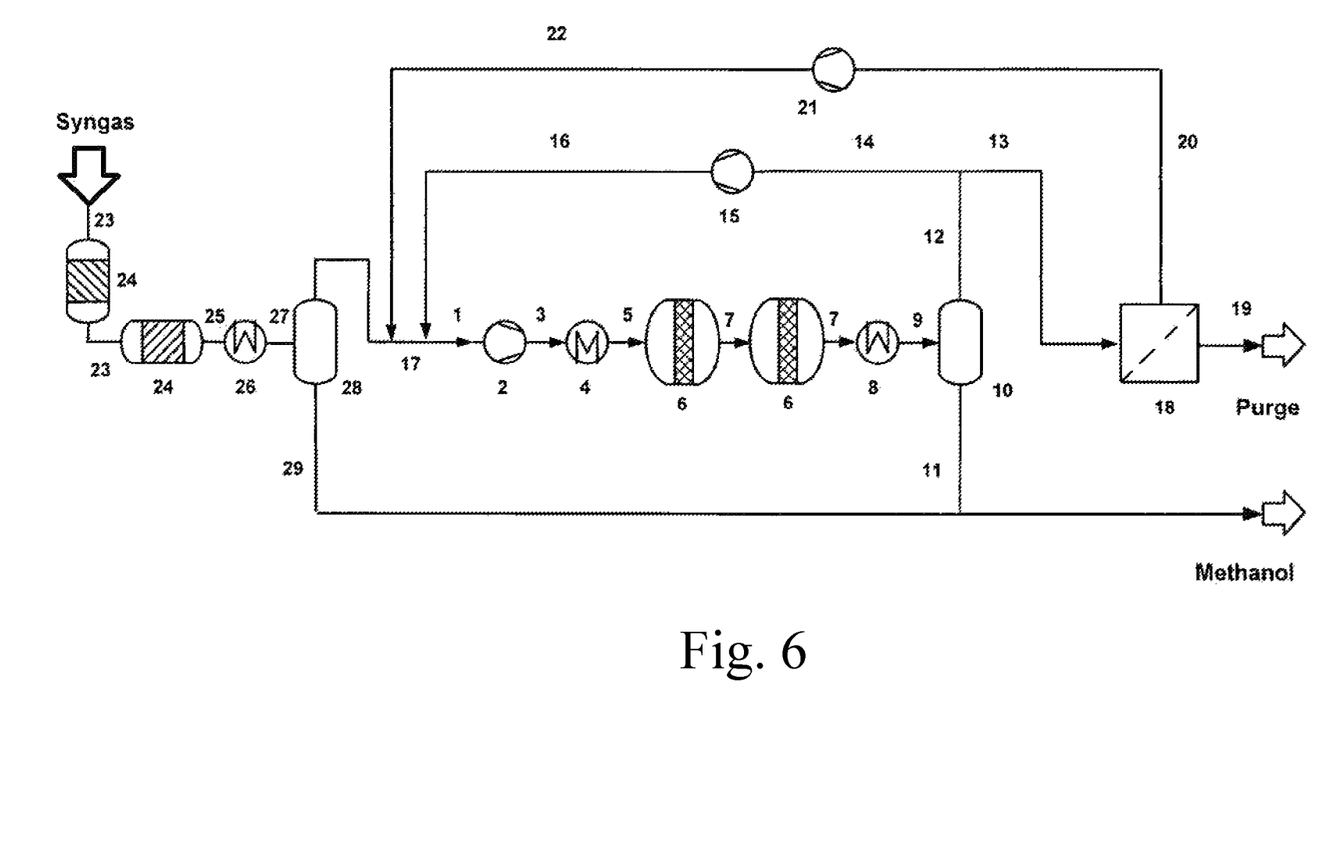
FIG. 6 schematically shows a plant for the production of methanol according to a fifth preferred embodiment of the invention, having a first and a second methanol reactor and a first and a second methanol main reactor.

FIG. 3 schematically shows a plant which represents a further preferred embodiment of the invention. This embodiment is preferred in particular when using coal-originating synthesis gas for the methanol synthesis, which can have a comparatively high methane content. In the gasification of coal in the fixed bed a synthesis gas is obtained, which can contain up to 60 vol-% of methane. In the plant shown in FIG. 3, as compared to FIG. 2, the purge stream leaving the pressure swing adsorption system 18 is not removed from the process, but via conduit 30 supplied an autothermal reformer 31, in which the methane enriched in the purge stream is converted to further synthesis gas. The mode of function and the operating conditions of the autothermal reformer also are known per se to the skilled person. A part of the product gas stream of the autothermal reformer is removed from the process as purge stream (purge) via conduit 19; a further part of the product gas stream of the autothermal reformer is supplied to the compressor 21 via conduit 32 and thereby joined with the synthesis gas stream supplied in conduit 20. In the conduit path 32 further processing stages not shown in the Figure can be provided for the synthesis gas. Thus, it is possible to first recirculate the synthesis gas partial stream in conduit 32 to the pressure swing adsorption system 18, in order to separate the hydrogen and recirculate the same via conduit 20 to the methanol main reactor. The hydrogen content in the outer synthesis cycle thereby is increased once again.

With the invention an economic process for the production of methanol thus is proposed, which is characterized in that it is also possible to process synthesis gases with a high content of inert components. In contrast to the processes proposed in the prior art, the process according to the invention is characterized by the absence of substances such as absorbents, which are foreign to the process or need to be disposed of or regenerated. Further advantages include the technical simplicity, small apparatus sizes and conduit dimensions, savings of catalyst and a lower energy demand, for example for the required compressor duty.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise. Moreover, the recitation of "A, B, and/or C" or "at least one of A, B, or C" should be interpreted as including any singular entity from the listed elements, e.g., A, any subset from the listed elements, e.g., A and B, or the entire list of elements A, B, and C.

LIST OF REFERENCE NUMERALS 1 conduit
2 compressor
3 conduit
4 heat exchanger
5 conduit
6 methanol main reactor(s)
7 conduit
8 heat exchanger
9 conduit
10 separator
11-14 conduit
15 compressor
16-17 conduit
18 pressure swing adsorption system
19-20 conduit
21 compressor
22-23 conduit
24 methanol pre-reactor(s)
25 conduit
26 heat exchanger
27 conduit
28 separator
29-30 conduit
31 autothermal reformer
32 conduit

The invention claimed is:
1. A plant for the production of methanol from a synthesis gas containing hydrogen, one or more carbon oxides, and one or more inert components, the plant comprising:
a methanol pre-reactor in which a first part of the carbon oxides is catalytically converted to methanol;
a methanol main reactor in which a second part of the carbon oxides is catalytically converted to methanol;
a first separator, downstream of the methanol pre-reactor, configured to separate the methanol from the synthesis gas;

a second separator, downstream of the methanol main reactor, configured to separate further methanol from the synthesis gas;

a conduit configured to recirculate a synthesis gas cycle stream to the methanol main reactor;

an inert gas separation stage;

a conduit configured to supply synthesis gas from the methanol main reactor to the inert gas separation stage;

a conduit configured to discharge a purge stream from the inert gas separation stage; and a conduit configured to recirculate a recirculation stream, depleted of one or more inert components, to the methanol main reactor.

2. The plant of claim 1, comprising:
the methanol pre-reactor as a first methanol pre-reactor; and
a second methanol pre-reactor.

3. The plant of claim 1, comprising:
the methanol main reactor as a first methanol main reactor; and
a second methanol main reactor.

4. The plant of claim 3, wherein the first methanol main reactor in flow direction is operated in a water-cooled manner, and
wherein the second methanol main reactor in flow direction is operated in a gas-cooled manner.

5. The plant of claim 1, wherein the inert gas separation stage comprises a pressure swing adsorption system.

6. The plant of claim 5, wherein the inert gas separation stage comprises an autothermal reformer.

7. The plant of claim 5, wherein the inert gas separation stage comprises an autothermal reformer and a pressure swing adsorption system.

8. The plant of claim 5, further comprising:
a natural gas gasification stage, configured to provide the first synthesis gas stream.

9. The plant of claim 5, further comprising:
a biomass gasification stage, configured to provide the first synthesis gas stream.

10. The plant of claim 5, further comprising:
a coal gasification stage, configured to provide the first synthesis gas stream.

11. The plant of claim 5, wherein the methanol main reactor is operated in a water-cooled manner.

12. The plant of claim 5, wherein the methanol main reactor is operated in an adiabatic manner.

13. The plant of claim 5, wherein the methanol main reactor is operated in a gas-cooled manner.

14. The plant of claim 1, wherein the inert gas separation stage comprises a membrane system.

15. The plant of claim 1, comprising:
the methanol pre-reactor as a first methanol pre-reactor;
a second methanol pre-reactor;
the methanol main reactor as a first methanol main reactor; and
a second methanol main reactor.

16. A method for retrofitting an existing plant for producing methanol with one or more methanol main reactors within an inner synthesis cycle from an operation with synthesis gas low in inerts to an operation with synthesis gas rich in inerts, in the plant of claim 1, the method comprising
providing, upstream of the methanol main reactor, the methanol pre-reactor;
providing, downstream of a last methanol main reactor, the inert gas separation stage, and
recirculating the synthesis gas cycle stream, depleted of one or more inert components, to the methanol main reactor, thereby forming an outer synthesis cycle,
wherein the methanol pre-reactor and the inert gas separation stage are located outside the inner synthesis cycle.

17. The method of claim 16, wherein the methanol obtained is supplied to the further product processing.

* * * * *